US012799053B2

(12) United States Patent
Chuang et al.

(10) Patent No.: US 12,799,053 B2
(45) Date of Patent: Nov. 17, 2026

(54) TRIBENZOTRIQUINACENE WITH AXIAL ARYL GROUP AND METHOD FOR PREPARING THE SAME

(71) Applicant: National Yang Ming Chiao Tung University, Hsinchu City (TW)

(72) Inventors: Shih-Ching Chuang, Hsinchu City (TW); Raju Selvam, Tamil Nadu (IN); Chun-Yu Chen, Taoyuan City (TW)

(73) Assignee: National Yang Ming Chiao Tung University, Hsinchu City (TW)

( * ) Notice: Subject to any disclaimer, the term of this patent is extended or adjusted under 35 U.S.C. 154(b) by 483 days.

(21) Appl. No.: 18/611,989

(22) Filed: Mar. 21, 2024

(65) Prior Publication Data

US 2025/0250215 A1 Aug. 7, 2025

(30) Foreign Application Priority Data

Feb. 1, 2024 (TW) ................................ 113104064

(51) Int. Cl.
*C07C 17/358* (2006.01)
*C07C 5/31* (2006.01)
(Continued)

(52) U.S. Cl.
CPC .............. *C07C 17/358* (2013.01); *C07C 5/31* (2013.01); *C07C 13/70* (2013.01); *C07C 25/22* (2013.01);
(Continued)

(58) Field of Classification Search
CPC ......... C07C 17/358; C07C 5/31; C07C 13/70; C07C 25/22; C07C 41/32; C07C 43/21; C07C 43/225; C07C 2603/92; C07C 13/64
See application file for complete search history.

(56) References Cited

U.S. PATENT DOCUMENTS 6,268,535 B1 7/2001 Moussa et al.

FOREIGN PATENT DOCUMENTS

CN 110433293 A 11/2019
CN 113773336 A 12/2021
(Continued)

OTHER PUBLICATIONS

Magic Acid—Safety Data Sheet (Pfaltz & Bauer Rare and Fine Chemicals) (Year: 2023).*
(Continued)

*Primary Examiner* — Amy C Bonaparte
*Assistant Examiner* — Derek Rhoades

(57) ABSTRACT

The present disclosure discloses tribenzotriquinacene with an axial aryl group and a method for preparing the same. The triphenyltripentacene has a structure shown in formula (1):

formula (1)

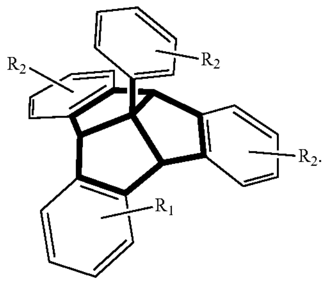

$R_1$ and $R_2$ are independently hydrogen, a C1-C12 alkyl group, a C1-C12 alkoxy group, a C1-C12 fluoroalkyl group, a C1-C12 fluorine-containing alkoxy group, a C1-C12 ester
(Continued)

group, a halogen group, a nitro group, an amine group, a cyano group, or a hydroxy group.

15 Claims, 1 Drawing Sheet

(51) Int. Cl.

| | |
|---|---|
| ***C07C 13/70*** | (2006.01) |
| ***C07C 25/22*** | (2006.01) |
| ***C07C 41/32*** | (2006.01) |
| ***C07C 43/21*** | (2006.01) |
| ***C07C 43/225*** | (2006.01) |

(52) U.S. Cl.

CPC .............. *C07C 41/32* (2013.01); *C07C 43/21* (2013.01); *C07C 43/225* (2013.01); *C07C 2603/92* (2017.05)

(56) References Cited

FOREIGN PATENT DOCUMENTS

| | | | | | |
|---|---|---|---|---|---|
| CN | 115216024 | A | | 10/2022 | |
| CN | 115448846 | A | | 12/2022 | |
| CN | 115449082 | A | | 12/2022 | |
| CN | 116675658 | A | | 9/2023 | |
| DE | 102006053070 | A1 | | 5/2008 | |
| JP | 2012180335 | A | | 9/2012 | |
| JP | 2013193972 | A | | 9/2013 | |
| JP | 2016074625 | A | | 5/2016 | |
| JP | 2017036322 | A | | 2/2017 | |
| TW | 201836614 | A | | 10/2018 | |
| WO | WO 2023/025230 | A1 | * | 2/2023 | ................ C07F 1/10 |

OTHER PUBLICATIONS

JP2013193972A (Naoki et al.; English language machine translation obtained from Espacenet on Sep. 8, 2026) (Year: 2026).*

WO 2023/025230 A1 (Tang et al.; English language machine translation obtained from Espacenet on Sep. 8, 2026) (Year: 2026).*

Kuck, Dietmar , et al., “Synthesis of Tribenzotriquinacene and Some centro-Substituted Derivatives”, Chem. Ber. 1992, 125, pp. 1449-1460.

Kuck, Dietmar , et al., “Synthesis of Tribenzotriquinacene by Stereocontrolled Cyclization of Phenyl-Substituted C,- Diindans (4bα,9,9aα,10-Tetrahydroindeno[ 1,2-α]indenes)”, Chem. Ber. 1994, 127, pp. 151-164.

Markopoulos, Georgios , et al., “Tribenzotriquinacene: A Versatile Synthesis and C3-Chiral Platforms”, Angewandte Chemie (International ed. in English), 2012, 51, pp. 12884-12887.

Zhang, Tao-Xiang , et al., Chinese Journal of Organic Chemistry, vol. 27, 2007, No. 8, 946-957, 2007, 12 pgs.

* cited by examiner

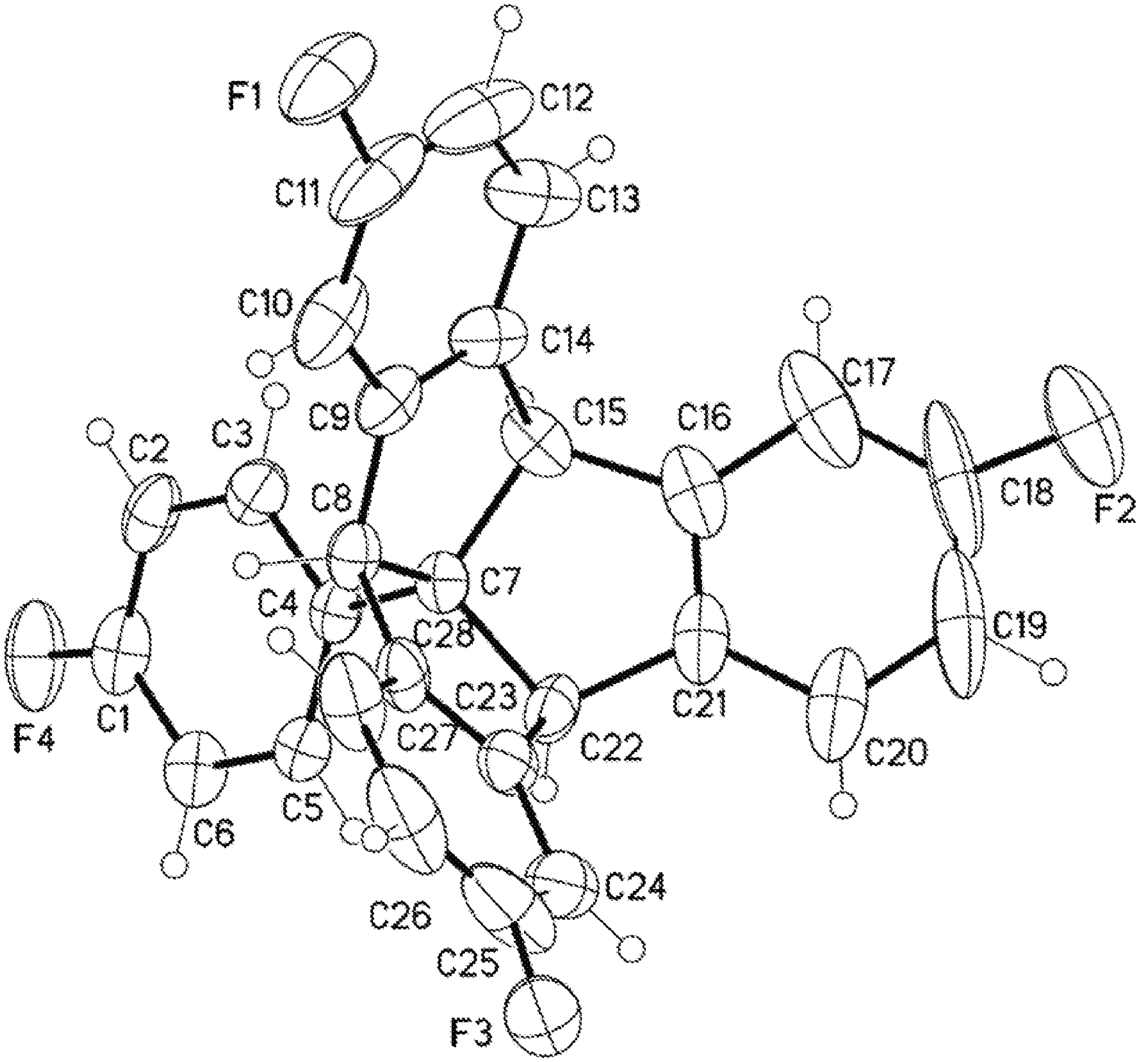

TRIBENZOTRIQUINACENE WITH AXIAL ARYL GROUP AND METHOD FOR PREPARING THE SAME

CROSS-REFERENCE TO RELATED APPLICATION

This application claims priority to Taiwan Application Serial Number 113104064, filed Feb. 1, 2024, which is herein incorporated by reference.

BACKGROUND

Field of Invention

The present disclosure relates to tribenzotriquinacene (TBTQ) with an axial aryl group and a method for preparing the same.

Description of Related Art

Tribenzotriquinacene is a bowl-shaped three-dimensional molecule with $C_{3v}$ symmetry. The tribenzotriquinacene has wide applicability due to the special three-dimensional configuration. For example, it can be applied to the preparation of organic nano-cubes, host-guest chemistry of $C_{60}$ molecules and $C_{70}$ molecules, the synthesis of microporous materials, and the assembly of large network molecules. However, methods for preparing the tribenzotriquinacene have the problem of low yield, and they are difficult to modify specific positions of the tribenzotriquinacene with functional groups, thereby limiting the applicability of tribenzotriquinacene.

SUMMARY

The present disclosure provides tribenzotriquinacene (TBTQ) with an axial aryl group. The tribenzotriquinacene has a structure shown in formula (1):

formula (1)

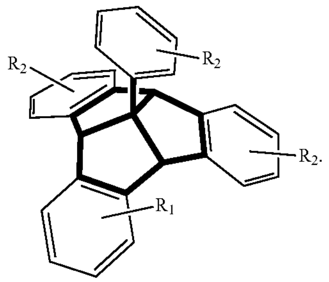

$R_1$ and $R_2$ are independently hydrogen, a C1-C12 alkyl group, a C1-C12 alkoxy group, a C1-C12 fluoroalkyl group, a C1-C12 fluorine-containing alkoxy group, a C1-C12 ester group, a halogen group, a nitro group (—$NO_2$), an amine group, a cyano group (—CN), or a hydroxy group (—OH).

In some embodiments, the tribenzotriquinacene has a structure shown in formula (2):

formula (2)

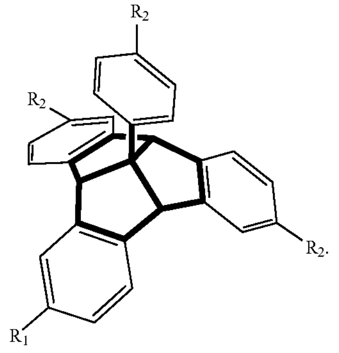

In some embodiments, the tribenzotriquinacene has a structure shown in formula (3):

formula (3)

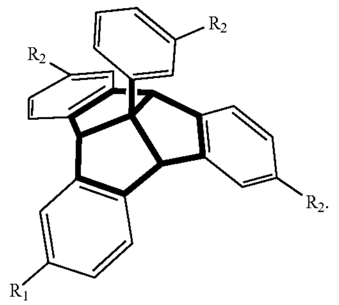

In some embodiments, $R_1$ and $R_2$ are independently hydrogen, a methyl group, an ethyl group, a n-propyl group, an isopropyl group, a n-butyl group, a sec-butyl group, a tert-butyl group, a n-pentyl group, an isopentyl group, a n-hexyl group, the nitro group, the amine group, a methoxy group, an ethoxy group, a trifluoromethyl group, a trifluoromethoxy group, a trifluoroethoxy group, a fluoro group, a chloro group, a bromo group, the cyano group, the hydroxy group, or —$CO_2CH_3$.

In some embodiments, $R_1$ and $R_2$ have the same structures.

In some embodiments, $R_1$ and $R_2$ have different structures.

The present disclosure provides a method of preparing tribenzotriquinacene with an axial aryl group, and the method includes reacting a reagent in the presence of a superacid to form the tribenzotriquinacene with the axial aryl group of any of the aforementioned embodiments. The reagent has a structure shown in formula (4):

formula (4)

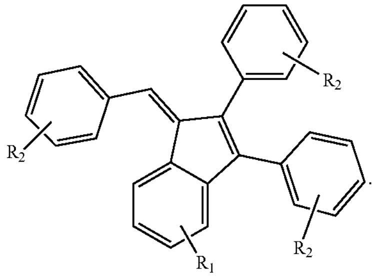

In some embodiments, the superacid includes trifluoromethanesulfonic acid (TfOH), fluorosulfuric acid ($HSO_3F$), fluoroantimonic acid, magic acid, carborane acid, or combinations thereof.

In some embodiments, a reaction time for reacting the reagent in the presence of the superacid is 1 hour to 24 hours.

In some embodiments, a reaction temperature for reacting the reagent in the presence of the superacid is 0 °C to 100 °C.

In some embodiments, the reaction temperature is 0 °C to 50 °C.

In some embodiments, the method further includes: before reacting the reagent in the presence of the superacid, adding the superacid and the reagent into a solvent, in which the solvent includes benzene, toluene, chlorobenzene, dichlorobenzene, dichloromethane (DCM), 1,2-dichloroethane, trichloromethane, or combinations thereof.

In some embodiments, the solvent is an anhydrous solvent.

In some embodiments, $R_1$ and $R_2$ have the same structures.

In some embodiments, $R_1$ and $R_2$ have different structures.

BRIEF DESCRIPTION OF THE DRAWINGS

The present disclosure can be more fully understood by reading the following detailed description of the embodiments, with reference made to the accompanying drawings.

The single FIGURE illustrates the crystal structure of X-ray single crystal diffraction of the tribenzotriquinacene having formula (a).

DETAILED DESCRIPTION

To make the description of the present disclosure more detailed and complete, the following provides an illustrative description of the embodiments and specific examples of the present disclosure; however, this is not the only form in which specific examples of the present disclosure are implemented or applied. The examples disclosed below may be combined or substituted for each other under useful circumstances, and other examples may be added to some examples without further recitation or description.

Although a series of operations or steps are used below to describe the method disclosed herein, an order of these operations or steps should not be construed as a limitation to the present disclosure. For example, some operations or steps may be performed in a different order, and/or other steps may be performed at the same time. In addition, it is not necessary to perform all of the operations, steps, and/or features shown to achieve the embodiments of the present disclosure. In addition, each operation or step described herein may contain several sub-steps or actions.

Tribenzotriquinacene has wide applicability and has huge development potential in the field of chemical research. In order to solve the problem that the yield of the preparation method of tribenzotriquinacene is not high, and it is difficult to modify specific positions (such as an axial position) of the tribenzotriquinacene with functional groups, the present disclosure provides tribenzotriquinacene (TBTQ) with an axial aryl group and its preparation method. The preparation method uses a reagent with a benzofulvene structure or a structure similar to benzofulvene as a reactant to synthesize the tribenzotriquinacene with the axial aryl group, which can also be called a tribenzotriquinacene-based compound with an axial aryl group. In other words, the apical position of the bowl-shaped structure of the tribenzotriquinacene is modified by an aryl group, thereby having the aryl group at the axial position. The preparation method has the advantages of simple process, mild reaction conditions, and high synthesis yield, and it can easily modify the axial position of the tribenzotriquinacene with an aryl group and easily modify the benzene ring of the tribenzotriquinacene, thereby improving the applicability of the tribenzotriquinacene. The tribenzotriquinacene with the axial aryl group can be applied to fields such as pharmaceutical industry, chemical industry (such as petrochemical industry), or biomedical industry, but is not limited thereto. For example, the tribenzotriquinacene can be applied to products such as natural essential oils, food additives, rubber, polymer materials, construction materials, computer and communication equipment, protective clothing, packaging materials, or biological detection platforms, but is not limited thereto.

The present disclosure provides tribenzotriquinacene with an axial aryl group. The tribenzotriquinacene has a structure shown in formula (1):

formula (1)

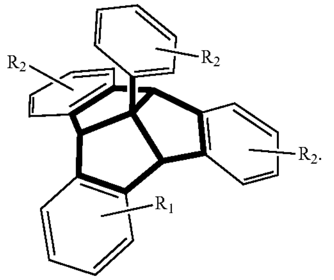

$R_1$ can be connected to any carbon atom of the benzene ring, and $R_2$ can be connected to any carbon atom of the benzene ring. $R_1$ and $R_2$ are independently hydrogen, a C1-C12 alkyl group, a C1-C12 alkoxy group, a C1-C12 fluoroalkyl group, a C1-C12 fluorine-containing alkoxy group, a C1-C12 ester group, a halogen group, a nitro group ($—NO_2$), an amine group, a cyano group (—CN), or a hydroxy group (—OH). For example, the carbon number of the C1-C12 alkyl group, the C1-C12 alkoxy group, the C1-C12 fluoroalkyl group, the C1-C12 fluorine-containing alkoxy group, and the C1-C12 ester group are respectively 1, 2, 3, 4, 5, 6, 7, 8, 9, 10, 11, or 12. In some embodiments, the C1-C12 alkyl group is a methyl group (-Me), an ethyl group (-Et), a n-propyl group, an isopropyl group, a n-butyl group, a sec-butyl group, a tert-butyl group, a n-pentyl group, an isopentyl group, or a n-hexyl group. In some embodiments, the C1-C12 alkoxy group is a methoxy group (—OMe) or an ethoxy group (—OEt). In some embodiments, the number of fluorine atoms in the C1-C12 fluoroalkyl group is 1, 2, 3, 4, 5, or 6, and the C1-C12 fluoroalkyl group is, for example, a trifluoromethyl group (—$CF_3$). In some embodiments, the number of fluorine atoms in the C1-C12 fluorine-containing alkoxy group is 1, 2, 3, 4, 5, or 6, and the C1-C12 fluorine-containing alkoxy group is, for example, a trifluoromethoxy group (—$OCF_3$) or a trifluoroethoxy group. In some embodiments, the C1-C12 ester group is —$CO_2R_a$, in which $R_a$ is a C1-C12 alkyl group, and the carbon number of the C1-C12 alkyl group is 1, 2, 3, 4, 5, 6, 7, 8, 9, 10, 11, or 12. In some embodiments, the C1-C12 ester group is —$CO_2CH_3$. In some embodiments, the halogen group is a fluoro group (—F), a chloro group (—Cl), or a bromo group (—Br). In some embodiments, the amine group is —$NH_2$, —$NHR_b$, or —$NR_bR_c$, in which $R_b$ and $R_c$ can be a C1-C12 alkyl group, and the carbon number of the C1-C12 alkyl group is 1, 2, 3, 4, 5, 6, 7, 8, 9, 10, 11, or 12. In some embodiments, $R_1$ and $R_2$ are independently hydrogen, a methyl group, an ethyl group, a n-propyl group, an isopropyl group, a n-butyl group, a sec-butyl group, a tert-butyl group, a n-pentyl group, an isopentyl group, a n-hexyl group, a nitro group, an amine group, a methoxy group, an ethoxy group, a trifluoromethyl group, a trifluoromethoxy group, a trifluoroethoxy group, a fluoro group, a chloro group, a bromo group, a cyano group, a hydroxy group, or —$CO_2CH_3$. In some embodiments, $R_1$ and $R_2$ have the same structures, and therefore the tribenzotriquinacene has high symmetry. In some embodiments, $R_1$ and $R_2$ have different structures.

In some embodiments, the tribenzotriquinacene has a structure shown in formula (2):

formula (2)

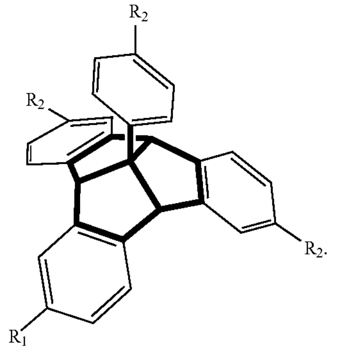

In some embodiments, the tribenzotriquinacene has a structure shown in formula (3):

formula (3)

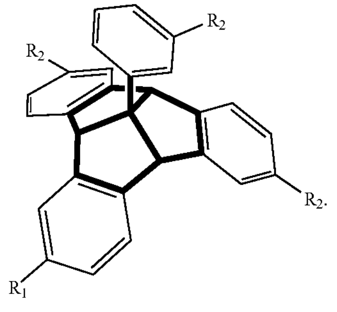

The present disclosure provides a method for preparing tribenzotriquinacene with an axial aryl group. This method includes reacting a reagent in the presence of a superacid to form the tribenzotriquinacene with the axial aryl group of any of the aforementioned embodiments. The reagent has a structure shown in formula (4):

formula (4)

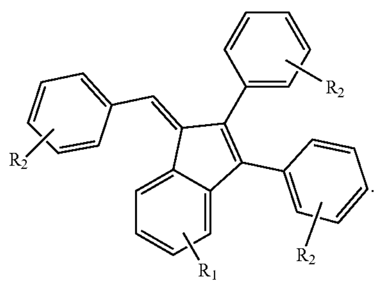

In more detail, the acid-mediated reaction between the superacid and the reagent occurs. The superacid can cause the reagent to be protonated and cyclized to generate the tribenzotriquinacene. The reagent has a benzofulvene structure or a structure similar to benzofulvene, which has the advantages of being easily synthesized, stable, inexpensive, and low toxicity. Moreover, since this reagent has no chiral center and has high purity, there is no need to consider that its stereometric structure will affect the synthesis reaction when using this reagent as a starting material to synthesize the tribenzotriquinacene. In addition, the benzene ring or bridgehead of this reagent can be easily modified with different functional groups ($R_1$, $R_2$), thereby expanding the applicability of the tribenzotriquinacene. In some embodiments, when reacting the reagent in the presence of the superacid, there is no need to add a transition metal catalyst, so the product is free of transition metals. The preparation method of the present disclosure has the advantages of simple process, mild reaction conditions, and high synthesis yield.

In some embodiments, the superacid includes trifluoromethanesulfonic acid, fluorosulfuric acid, fluoroantimonic acid, magic acid, carborane acid, or combinations thereof, in which the trifluoromethanesulfonic acid has a non-perishable property. In some embodiments, a reaction time for reacting the reagent in the presence of the superacid is 1 hour to 24 hours. For example, the reaction time is 1, 2, 4, 6, 8, 10, 12, 14, 16, 18, 20, 22, or 24 hours. In some embodiments, a reaction temperature for reacting the reagent in the presence of the superacid is 0 °C to 100 °C. For example, the reaction temperature is 0, 10, 20, 30, 40, 50, 60, 70, 80, 90, or 100 °C. It can be known that the preparation method of the present disclosure has the advantages of simple process and mild reaction conditions.

In some embodiments, the method further includes: before reacting the reagent in the presence of the superacid, adding the superacid and the reagent into a solvent, in which the solvent includes benzene, toluene, chlorobenzene, dichlorobenzene, dichloromethane, 1,2-dichloroethane, trichloromethane, or combinations thereof. In some embodiments, the solvent is an anhydrous solvent.

Next, the connection positions of $R_1$ and $R_2$ in the reagent are further described. In the structure of formula (4), the carbon atoms on the benzene ring are numbered. Please refer to the following formula (4-1):

formula (4-1)

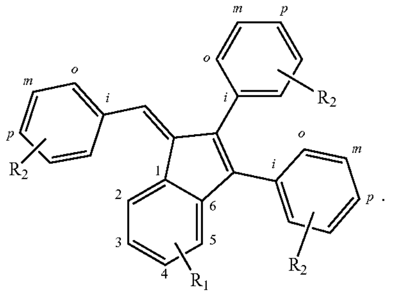

In formula (4-1), $R_1$ can be connected to any carbon atom of the benzene ring, and $R_2$ can be connected to any carbon atom of the benzene ring. In more detail, $R_1$ can be bonded to the carbon atom numbered as 1, 2, 3, 4, 5, or 6. These $R_2$ on different benzene rings are respectively bonded to the carbon atom numbered as i, o, m, or p. These $R_2$ can all be bonded to the same numbered carbons, or these $R_2$ can be bonded to different numbered carbons.

In some embodiments, in the reagent having the structure shown in formula (4-1), $R_1$ is bonded to the carbon numbered as 3, and $R_2$ are bonded to the carbons numbered as p, so the reagent has a structure shown in formula (5):

formula (5)

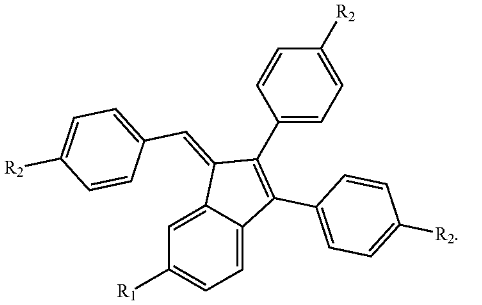

In the presence of the superacid, the reagent having the structure shown in formula (5) can react to form the tribenzotriquinacene having the structure shown in formula (2).

In some embodiments, in the reagent with the structure shown in formula (4-1), $R_1$ is bonded to the carbon numbered as 3, and $R_2$ is bonded to the carbon numbered as m, so the reagent has a structure shown in formula (6):

formula (6)

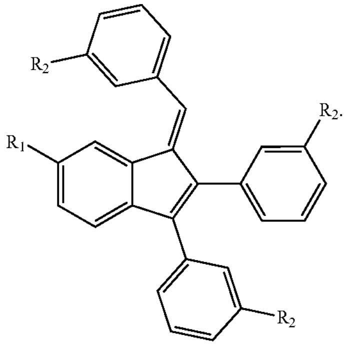

In the presence of the superacid, the reagent having the structure shown in formula (6) can react to form the tribenzotriquinacene having the structure shown in formula (3).

The following describes the features of the present disclosure more specifically with reference to Experimental Examples 1 to 10. Although the following Experimental Examples are described, the materials, their amounts and ratios, processing details, processing procedures, etc., may be appropriately varied without exceeding the scope of the present disclosure. Accordingly, the present disclosure should not be interpreted restrictively by the Experimental Examples described below.

Experimental Example 1: Synthesis of Tribenzotriquinacene with Formula (a)

A 25 mL glass tube equipped with a stir bar was charged with the reagent (0.1 mmol) having the structure shown in formula (5), TfOH (0.1 mL, 20 equivalents), and DCM (1.0 mL) to form a reaction mixture. In formula (5), both $R_1$ and $R_2$ are fluoro groups (—F), so the reagent has a structure shown in the following formula (5-1):

formula (5-1)

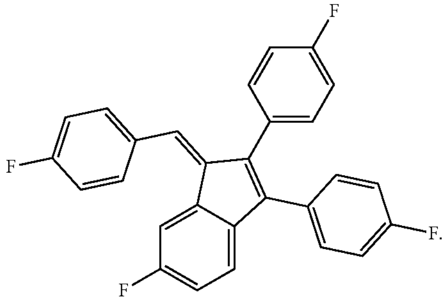

The glass tube is sealed with a screw cap in an air atmosphere, and the reaction mixture is stirred at room temperature (30 °C) for 24 hours. In more detail, the TfOH-mediated reaction between the TfOH and the reagent occurs. Then, the reaction mixture was quenched with crushed ice, and then with ice-cold sodium bicarbonate aqueous solution. Next, the product was extracted with DCM. The residue was obtained by removing the DCM under reduced pressure, and the residue was purified by flash column chromatography, in which the eluent included hexane and ethyl acetate, and the volume ratio of the hexane to the ethyl acetate was 50:1. After purification, the product was obtained and it had a structure shown in the following formula (a):

formula (a)

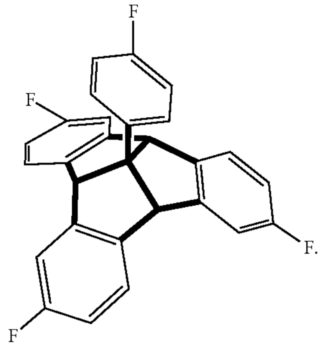

The product was a white solid, and the crude yield was 91%. After purification, the product weight was 31.6 mg, and the product yield was 74%. The melting point of the product was 242 °C to 246 °C. When hexane was used as the developing solution, the $R_f$ value of the product was 0.26. The chemical shifts (δ) (unit: ppm) of the nuclear magnetic resonance (NMR) hydrogen spectrum ($^1$H-NMR ($CDCl_3$, 400 MHz)) of the product is 7.40-7.35 (m, 5H), 7.14 (dd, J=2.0, 8.8 Hz, 3H), 7.07-7.02 (m, 2H), 6.99 (td, J=2.4, 88 Hz, 3H), 5.00 (s, 3H). The chemical shifts (δ) (unit: ppm) of the NMR carbon spectrum of the product ($^{13}$C NMR ($CDCl_3$, 100 MHz)) are 164.3 (d, $^1J_{C-F}$=244.0 Hz), 161.8 (d, $^1J_{C-F}$=244.4 Hz), 146.6 (d, $^3J_{C-F}$=7.6 Hz), 143.7 (d, $^4J_{C-F}$=3.4 Hz), 139.5 (d, $^4J_{C-F}$=2.6 Hz), 126.4 (d, $^3J_{C-F}$=7.6 Hz), 125.3 (d, $^3J_{C-F}$=8.8 Hz), 115.8 (d, $^2J_{C-F}$=21.3 Hz), 115.3 (d, $^2J_{C-F}$=22.8 Hz), 111.0 (d, $^2J_{C-F}$=22.1 Hz), 70.7, 63.4 (d, $^4J_{C-F}$=1.9 Hz). The product and KBr were mixed to prepare a sample, and the Fourier-transform infrared spectroscopy (FTIR) of spectrum of the sample was measured. The wave numbers (unit: $cm^{-1}$) corresponding to the wave peaks in the spectrum are 3067, 2870, 1608, 1279, 1096, 964. The theoretical value of the molecular weight of the product is 428.1188. The molecular weight of the product was 428.1191, which could be measured by high resolution mass spectrometer (HRMS) and is quite close to the theoretical value. The crystal structure of X-ray single crystal diffraction of the tribenzotriquinacene having formula (a) is shown in the single FIGURE. The above test results can prove that Experimental Example 1 can prepare the tribenzotriquinacene with formula (a), and its structure is named (4bR,8bR,12bR)-2,6,10-trifluoro-4b$^1$-(4-fluorophenyl)-4b,4b$^1$,8b,12b-tetrahydrodibenzo[2,3:4,5]pentaleno[1,6-ab]indene.

Experimental Example 2: Synthesis of Tribenzotriquinacene with Formula (b)

Please refer to the preparation process of Experimental Example 1 to synthesize the tribenzotriquinacene with the following formula (b). In Experimental Example 2, the reagent has the structure shown in formula (5), and both $R_1$ and $R_2$ are hydrogens (—H).

formula (b)

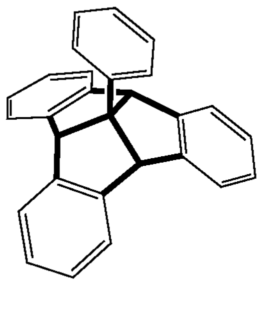

The product was a white solid, and the crude yield was 98%. After purification, the product weight was 25.6 mg, and the product yield was 72%. The melting point of the product was 230 °C to 232 °C. When hexane was used as the developing solution, the $R_f$ value of the product was 0.25. The chemical shifts (δ) (unit: ppm) of the nuclear magnetic resonance (NMR) hydrogen spectrum ($^1$H-NMR ($CDCl_3$, 400 MHz)) of the product are 7.50-7.45 (m, 8H), 7.34 (t, J=7.6 Hz, 2H), 7.28-7.20 (m, 7H), 5.16 (s, 3H). The chemical shifts (δ) (unit: ppm) of the NMR carbon spectrum of the product ($^{13}$C NMR ($CDCl_3$, 100 MHz)) are 149.0, 145.0, 128.9, 127.7, 126.3, 125.1, 124.1, 68.9, 64.3. The product and KBr were mixed to prepare a sample, and the FTIR spectrum of the sample was measured. The wave numbers (unit: $cm^{-1}$) corresponding to the wave peaks in the spectrum are 3054, 2924, 1587, 1267, 1013. The theoretical value of the molecular weight of the product is 356.1565. The molecular weight of the product was 356.1568, which could be measured by HRMS and is quite close to the theoretical value. The above test results can prove that Experimental Example 2 can prepare the tribenzotriquinacene with formula (b), and its structure is named (4bR, 8bR,12bR)-4b$^1$-phenyl-4b,4b$^1$,8b,12b-tetrahydrodibenzo[2, 3:4,5]pentaleno [1,6-ab]indene.

Experimental Example 3: Synthesis of Tribenzotriquinacene with Formula (c)

Please refer to the preparation process of Experimental Example 1 to synthesize the tribenzotriquinacene with the following formula (c). In Experimental Example 3, the reagent has the structure shown in formula (5), and both $R_1$ and $R_2$ are chloro groups (—Cl).

formula (c)

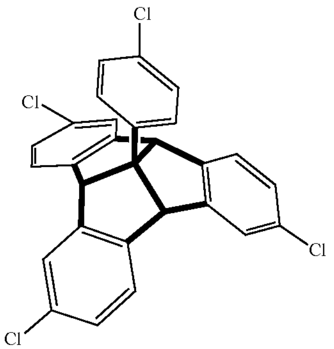

The product was a white solid, and the crude yield was 95%. After purification, the product weight was 35.9 mg, and the product yield was 73%. The melting point of the product was 230 °C to 232 °C. When hexane was used as the developing solution, the $R_f$ value of the product was 0.25. The chemical shifts (δ) (unit: ppm) of the nuclear magnetic resonance (NMR) hydrogen spectrum ($^1$H-NMR ($CDCl_3$, 400 MHz)) of the product are 7.39 (s, 3H), 7.37 (d, J=8.4 Hz, 3H), 7.33-7.28 (m, 4H), 7.24 (dd, J=1.8, 8.0 Hz, 3H), 4.98 (s, 3H). The chemical shifts (δ) (unit: ppm) of the NMR carbon spectrum of the product (13C NMR ($CDCl_3$, 100 MHz)) are 146.1, 146.0, 142.2, 134.0, 132.5, 129.1, 128.4, 126.2, 125.3, 124.2, 69.9, 63.3. The product and KBr were mixed to prepare a sample, and the FTIR spectrum of the sample was measured. The wave numbers (unit: $cm^{-1}$) corresponding to the wave peaks in the spectrum are 3054, 2923, 1373, 1012, 954. The theoretical value of the molecular weight of the product is 492.0006. The molecular weight of the product was 492.0011, which could be measured by HRMS and is quite close to the theoretical value. The above test results can prove that Experimental Example 3 can prepare the tribenzotriquinacene with formula (c), and its structure is named (4bR,8bR,12bR)-2,6,10-trichloro-4b$^1$-(4-chlorophenyl)-4b,4b$^1$,8b,12b-tetrahydro dibenzo[2,3:4,5] pentaleno[1,6-ab]indene.

Experimental Example 4: Synthesis of Tribenzotriquinacene with Formula (d)

Please refer to the preparation process of Experimental Example 1 to synthesize the tribenzotriquinacene with the following formula (d). In Experimental Example 4, the reagent has the structure shown in formula (5), and both $R_1$ and $R_2$ are bromo groups (—Br).

formula (d)

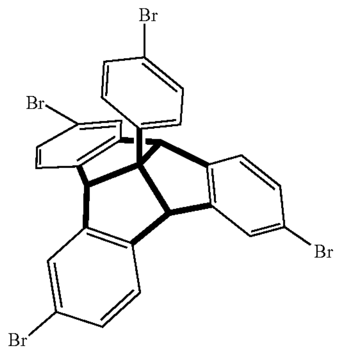

The product was a white solid, and the crude yield was 98%. After purification, the product weight was 53.4 mg, and the product yield was 80%. The melting point of the product was 250 °C to 252 °C. When hexane was used as the developing solution, the $R_f$ value of the product was 0.26. The chemical shifts (δ) (unit: ppm) of the nuclear magnetic resonance (NMR) hydrogen spectrum ($^1$H-NMR ($CDCl_3$, 400 MHz)) of the product is 7.54 (s, 3H), 7.49 (td, J=2.4, 9.2 Hz, 2H), 7.40 (dd, J=1.2, 8.0 Hz, 3H), 7.32 (d, J=8.0 Hz, 3H), 7.24 (td, J=2.4, 9.8 Hz, 2H), 4.96 (s, 3H). The chemical shifts (δ) (unit: ppm) of the NMR carbon spectrum of the product ($^{13}$C NMR ($CDCl_3$, 100 MHz)) are 146.5, 146.2, 142.7, 132.1, 131.3, 127.2, 126.6, 125.7, 122.0, 120.6, 69.6, 63.3. The product and KBr were mixed to prepare a sample, and the FTIR spectrum of the sample was measured. The wave numbers (unit: $cm^{-1}$) corresponding to the wave peaks in the spectrum are 3021, 2850, 1894, 1062, 953. The theoretical value of the molecular weight of the product is 667.7986. The molecular weight of the product was 667.7992, which could be measured by HRMS and is quite close to the theoretical value. The above test results can prove that Experimental Example 4 can prepare the tribenzotriquinacene with formula (d), and its structure is named (4bR,8bR,12bR)-2,6,10-tribromo-4b$^1$-(4-bromophenyl)-4b, 4b$^1$,8b,12b-tetrahydro dibenzo[2,3:4,5]pentaleno[1,6-ab]indene.

Experimental Example 5: Synthesis of Tribenzotriquinacene with Formula (e)

Please refer to the preparation process of Experimental Example 1 to synthesize the tribenzotriquinacene with the following formula (e). In Experimental Example 5, the reagent has the structure shown in formula (5), and both $R_1$ and $R_2$ are trifluoromethoxy groups (—$OCF_3$).

formula (e)

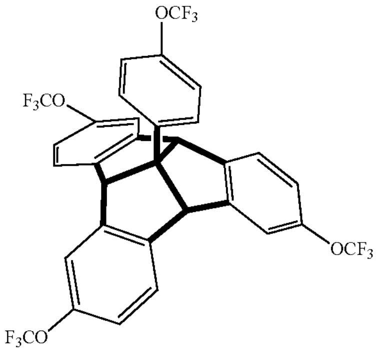

The product was a white solid, and the crude yield was 95%. After purification, the product weight was 56.1 mg, and the product yield was 81%. The melting point of the product was 218 °C to 220 °C. When hexane was used as the developing solution, the $R_f$ value of the product was 0.24. The chemical shifts (δ) (unit: ppm) of the nuclear magnetic resonance (NMR) hydrogen spectrum ($^1$H-NMR ($CDCl_3$, 400 MHz)) of the product are 7.50 (d, J=8.4 Hz, 3H), 7.46 (dd, J=2.0, 6.8 Hz, 2H), 7.33 (s, 3H), 7.26 (d, J=6.8 Hz, 2H), 7.19 (d, J=9.6 Hz, 3H), 5.12 (s, 3H). The chemical shifts (5) (unit: ppm) of the NMR carbon spectrum of the product ($^{13}$C NMR ($CDCl_3$, 100 MHz)) are 149.5, 149.5, 148.0, 146.1, 146.0, 142.3, 127.3 (q, $J_{C-F}$=297.5 Hz), 125.2, 124.3 (q, $J_{C-F}$=256.1 Hz), 121.1, 119.2, 117.0, 70.5, 63.4. The product and KBr were mixed to prepare a sample, and the FTIR spectrum of the sample was measured. The wave numbers (unit: $cm^{-1}$) corresponding to the wave peaks in the spectrum are 2956, 2849, 1905, 1160, 985. The theoretical value of the molecular weight of the product is 692.0857. The molecular weight of the product was 692.0852, which could be measured by HRMS and is quite close to the theoretical value. The above test results can prove that Experimental Example 5 can prepare the tribenzotriquinacene with formula (e), and its structure is named (4bR,8bR,12bR)-2,6,10-tris(trifluoromethoxy)-4b$^1$-(4-(trifluoromethoxy)phenyl)-4b,4b1,8b,12b-tetrahydrodibenzo[2,3:4,5]pentaleno[1,6-ab]indene.

Experimental Example 6: Synthesis of Tribenzotriquinacene with Formula (f)

Please refer to the preparation process of Experimental Example 1 to synthesize the tribenzotriquinacene with the following formula (f). In Experimental Example 6, the reagent has the structure shown in formula (5), and both $R_1$ and $R_2$ are methyl groups (-Me).

formula (f)

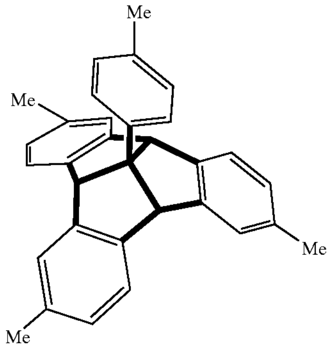

The product was a white solid, and the crude yield was 49%. After purification, the product weight was 13.1 mg, and the product yield was 32%. The melting point of the product is 226 °C to 228 °C. When hexane was used as the developing solution, the $R_f$ value of the product was 0.34. The chemical shifts (δ) (unit: ppm) of the nuclear magnetic resonance (NMR) hydrogen spectrum ($^1$H-NMR ($CDCl_3$, 400 MHz)) of the product are 7.17-7.12 (m, 7H), 7.11-7.09 (m, 3H), 6.95 (s, 3H), 4.81 (s, 3H), 2.34 (s, 6H), 2.29 (s, 6H). The chemical shifts (δ) (unit: ppm) of the NMR carbon spectrum of the product ($^{13}$C NMR ($CDCl_3$, 175 MHz)) are 153.1, 153.0, 137.1, 136.4, 136.2, 134.7, 129.5, 128.0, 127.4, 125.4, 119.0, 50.5, 21.5, 21.1. The product and KBr were mixed to prepare a sample, and the FTIR spectrum of the sample was measured. The wave numbers (unit: $cm^{-1}$) corresponding to the wave peaks in the spectrum are 2920, 2730, 1940, 1413, 966. The theoretical value of the molecular weight of the product is 412.2191. The molecular weight of the product was 412.2196, which could be measured by HRMS and is quite close to the theoretical value. The above test results can prove that Experimental Example 6 can prepare the tribenzotriquinacene with formula (f), and its structure is named (4bR,8bR,12bR)-2,6,10-trimethyl-4b$^1$-(p-tolyl)-4b,4b$^1$,8b,12b-tetrahydrodibenzo[2,3:4,5]pentaleno[1,6-ab]indene.

Experimental Example 7: Synthesis of Tribenzotriquinacene with Formula (g)

Please refer to the preparation process of Experimental Example 1 to synthesize the tribenzotriquinacene with the following formula (g). In Experimental Example 7, the reagent has the structure shown in formula (5), and both $R_1$ and $R_2$ are methoxy groups (—OMe).

formula (g)

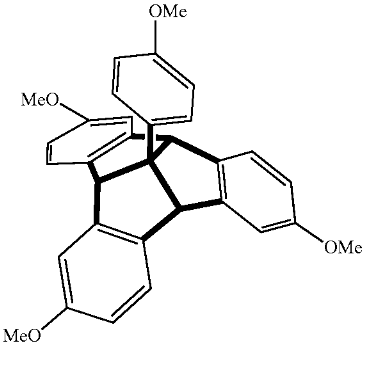

The product was a white solid, and the crude yield was 61%. After purification, the product weight was 24.7 mg, and the product yield was 52%. The melting point of the product was 226 °C to 228 °C. When hexane was used as the developing solution, the $R_f$ value of the product was 0.34. The chemical shifts (δ) (unit: ppm) of the nuclear magnetic resonance (NMR) hydrogen spectrum ($^1$H-NMR ($CDCl_3$, 400 MHz)) of the product are 7.17-7.12 (m, 7H), 7.11-7.09 (m, 3H), 6.95 (s, 3H), 4.81 (s, 3H), 2.34 (s, 6H), 2.29 (s, 6H). The chemical shifts (δ) (unit: ppm) of the NMR carbon spectrum of the product ($^{13}$C NMR ($CDCl_3$, 175 MHz)) are 159.7, 146.9, 141.3, 136.9 (2C), 126.0, 124.6, 114.1, 113.5, 109.2, 70.4, 63.6, 55.5, 55.3. The product and KBr were mixed to prepare a sample, and the FTIR spectrum of the sample was measured. The wave numbers (unit: $cm^{-1}$) corresponding to the wave peaks in the spectrum are 2920, 2730, 1940, 1413, 966. The theoretical value of the molecular weight of the product is 476.1988. The molecular weight of the product was 476.1995, which could be measured by HRMS and is quite close to the theoretical value. The above test results can prove that Experimental Example 7 can prepare the tribenzotriquinacene with formula (g), and its structure is named (4bR,8bR,12bR)-2,6,10-trimethoxy-4b$^1$-(4-methoxyphenyl)-4b,4b$^1$,8b,12b-tetrahydrodibenzo[2,3:4,5]pentaleno[1,6-ab]indene.

Experimental Example 8: Synthesis of Tribenzotriquinacene with Formula (h)

Please refer to the preparation process of Experimental Example 1 to synthesize the tribenzotriquinacene with the following formula (h). In Experimental Example 8, the reagent has the structure shown in formula (5), and both $R_1$ and $R_2$ are isopropyl groups (—$^i$Pr).

formula (h)

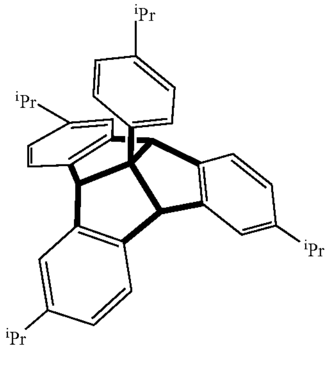

The product was a white solid, and the crude yield was 52%. After purification, the product weight was 23.5 mg, and the product yield was 45%. The melting point of the product was 198 °C to 200 °C. When hexane was used as the developing solution, the $R_f$ value of the product was 0.35. The chemical shifts (δ) (unit: ppm) of the nuclear magnetic resonance (NMR) hydrogen spectrum ($^1$H-NMR ($CDCl_3$, 400 MHz)) of the product are 7.38 (s, 5H), 7.29 (d, J=10.8 Hz, 3H), 7.16 (d, J=7.6 Hz, 2H), 7.08 (d, J=7.6 Hz, 3H), 5.06 (s, 3H), 2.91-2.84 (m, 4H), 1.40-1.20 (m, 24H). The chemical shifts (δ) (unit: ppm) of the NMR carbon spectrum of the product ($^{13}$C NMR ($CDCl_3$, 175 MHz)) are 148.2, 146.7, 146.6, 142.6, 126.3, 125.9, 125.8, 125.4, 123.8, 121.8, 69.5, 63.9, 34.1, 33.9, 33.6, 24.2, 24.0, 23.9. The product and KBr were mixed to prepare a sample, and the FTIR spectrum of the sample was measured. The wave numbers (unit: $cm^{-1}$) corresponding to the wave peaks in the spectrum are 2870, 1708, 1432, 1155, 1039, 778. The theoretical value of the molecular weight of the product is 524.3443. The molecular weight of the product was 524.3442, which could be measured by HRMS and is quite close to the theoretical value. The above test results can prove that Experimental Example 8 can prepare the tribenzotriquinacene with formula (h), and its structure is named (4bR,8bR,12bR)-2,6,10-triisopropyl-$4b^1$-(4-isopropylphenyl)-4b,$4b^1$,8b,12b-tetrahydrodibenzo[2,3:4,5]pentaleno[1,6-ab]indene.

Experimental Example 9: Synthesis of Tribenzotriquinacene with Formula (i)

Please refer to the preparation process of Experimental Example 1 to synthesize the tribenzotriquinacene with the following formula (i). In Experimental Example 9, the reagent has the structure shown in formula (6), and both $R_1$ and $R_2$ are chloro groups (—Cl).

formula (i)

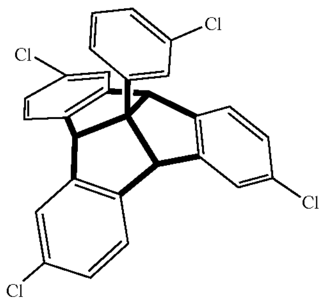

The product was a white solid, and the crude yield was 45%. After purification, the product weight was 20.2 mg, and the product yield was 41%. The melting point of the product was 212 °C to 214 °C. When hexane was used as the developing solution, the $R_f$ value of the product was 0.31. The chemical shifts (δ) (unit: ppm) of the nuclear magnetic resonance (NMR) hydrogen spectrum ($^1$H-NMR ($CDCl_3$, 400 MHz)) of the product are 7.28-7.24 (m, 3H), 7.19 (d, J=7.6 Hz, 2H), 7.12-7.09 (m, 6H), 7.04-7.02 (m, 2H), 4.90 (s, 3H). The chemical shifts (δ) (unit: ppm) of the NMR carbon spectrum of the product ($^{13}$C NMR ($CDCl_3$, 100 MHz)) are 154.1, 150.2, 140.2, 139.6, 134.9, 133.5 (2C), 130.4, 127.8, 126.2, 125.9, 120.0, 56.4, 50.2. The product and KBr were mixed to prepare a sample, and the FTIR spectrum of the sample was measured. The wave numbers (unit: $cm^{-1}$) corresponding to the wave peaks in the spectrum are 3121, 2891, 1542, 1112, 932. The theoretical value of the molecular weight of the product is 492.0006. The molecular weight of the product was 492.0001, which could be measured by HRMS and is quite close to the theoretical value. The above test results can prove that Experimental Example 9 can prepare the tribenzotriquinacene with formula (i), and its structure is named (4bS,8bS,12bS)-2,6,10-trichloro-$4b^1$-(3-chlorophenyl)-4b,$4b^1$,8b,12b-tetrahydrodibenzo[2,3:4,5]pentaleno[1,6-ab]indene.

Experimental Example 10: Synthesis of Tribenzotriquinacene with Formula (j)

Please refer to the preparation process of Experimental Example 1 to synthesize the tribenzotriquinacene with the following formula (j). In Experimental Example 10, the reagent has the structure shown in formula (6), and both $R_1$ and $R_2$ are methoxy groups (—OMe).

formula (j)

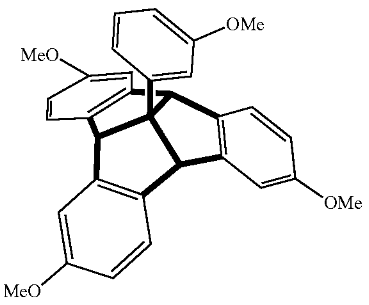

The product was a white solid, and the crude yield was 58%. After purification, the product weight was 20.5 mg, and the product yield was 43%. The melting point of the product was 242 °C to 244 °C. When hexane was used as the developing solution, the $R_f$ value of the product was 0.11. The chemical shifts (δ) (unit: ppm) of the nuclear magnetic resonance (NMR) hydrogen spectrum ($^1$H-NMR ($CDCl_3$, 400 MHz)) of the product are 7.34 (d, J=8.4 Hz, 3H), 7.24 (d, J=8.0 Hz, 1H), 7.02 (d, J=7.6 Hz, 1H), 6.98 (s, 1H), 6.94 (s, 3H), 6.77-6.72 (m, 4H), 4.98 (s, 3H), 3.78 (s, 9H), 3.74 (s, 3H). The chemical shifts (δ) (unit: ppm) of the NMR carbon spectrum of the product ($^{13}$C NMR ($CDCl_3$, 100 MHz)) are 160.0, 159.7, 150.8, 146.8, 136.8, 129.8, 124.6, 117.5, 113.6, 111.8, 110.5, 109.2, 71.0, 63.4, 55.5, 55.2. The product and KBr were mixed to prepare a sample, and the FTIR spectrum of the sample was measured. The wave numbers (unit: $cm^{-1}$) corresponding to the wave peaks in the spectrum are 3066, 2853, 1332, 1023, 962. The theoretical value of the molecular weight of the product is 476.1988. The molecular weight of the product was 476.1985, which could be measured by HRMS and is quite close to the theoretical value. The above test results can prove that Experimental Example 10 can prepare the tribenzotriquinacene with formula (j), and its structure is named (4bS, 8bS,12bS)-2,6,10-trimethoxy-$4b^1$-(3-methoxyphenyl)-4b, $4b^1$,8b,12b-tetrahydrodibenzo[2,3:4,5]pentaleno[1,6-ab]indene.

In summary, the present disclosure provides tribenzotriquinacene with an axial aryl group and a preparation method thereof. The preparation method has the advantages of simple process, mild reaction conditions, and high synthesis yield. It can easily modify the axial position of the tribenzotriquinacene with an aryl group and the benzene ring of the tribenzotriquinacene, thereby expanding the applicability of the tribenzotriquinacene.

Although the present disclosure has been described in considerable detail with reference to certain embodiments, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the present disclosure. In view of the foregoing, it is intended that the present disclosure cover the modifications and variations of the present disclosure falling within the scope of the appended claims.

What is claimed is:

1. Tribenzotriquinacene with an axial aryl group, having a structure shown in formula (1):

formula (1)

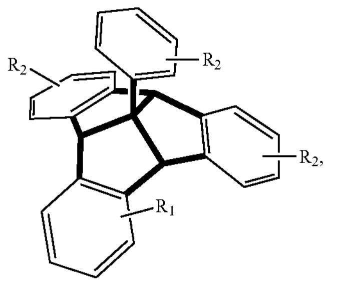

wherein $R_1$ and $R_2$ are independently hydrogen, a C1-C12 alkyl group, a C1-C12 alkoxy group, a C1-C12 fluoroalkyl group, a C1-C12 fluorine-containing alkoxy group, a C1-C12 ester group, a halogen group, a nitro group, an amine group, a cyano group, or a hydroxy group.

2. The tribenzotriquinacene with the axial aryl group of claim 1, wherein the tribenzotriquinacene has a structure shown in formula (2):

formula (2)

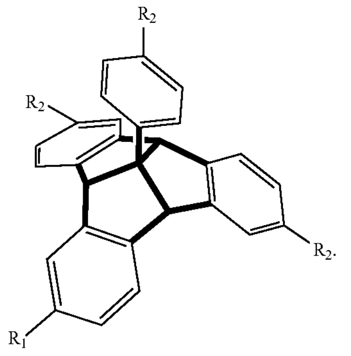

3. The tribenzotriquinacene with the axial aryl group of claim 1, wherein the tribenzotriquinacene has a structure shown in formula (3):

formula (3)

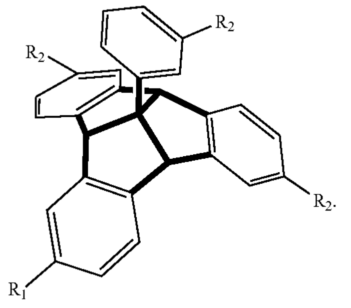

4. The tribenzotriquinacene with the axial aryl group of claim 1, wherein $R_1$ and $R_2$ are independently hydrogen, a methyl group, an ethyl group, a n-propyl group, an isopropyl group, a n-butyl group, a sec-butyl group, a tert-butyl group, a n-pentyl group, an isopentyl group, a n-hexyl group, the nitro group, the amine group, a methoxy group, an ethoxy group, a trifluoromethyl group, a trifluoromethoxy group, a trifluoroethoxy group, a fluoro group, a chloro group, a bromo group, the cyano group, the hydroxy group, or $-CO_2CH_3$.

5. The tribenzotriquinacene with the axial aryl group of claim 1, wherein $R_1$ and $R_2$ have the same structures.

6. The tribenzotriquinacene with the axial aryl group of claim 1, wherein $R_1$ and $R_2$ have different structures.

7. A method of preparing the tribenzotriquinacene with the axial aryl group of claim 1, comprising:

reacting a reagent in the presence of a superacid to form the tribenzotriquinacene with the axial aryl group of claim 1, wherein the reagent has a structure shown in formula (4):

formula (4)

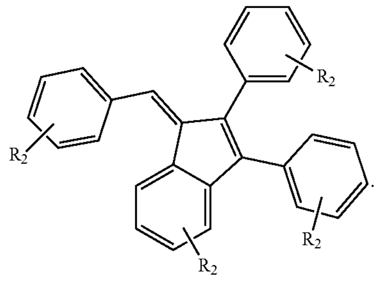

8. The method of claim 7, wherein the superacid comprises trifluoromethanesulfonic acid, fluorosulfuric acid, fluoroantimonic acid, magic acid, carborane acid, or combinations thereof.

9. The method of claim 7, wherein a reaction time for reacting the reagent in the presence of the superacid is 1 hour to 24 hours.

10. The method of claim 7, wherein a reaction temperature for reacting the reagent in the presence of the superacid is 0 °C to 100 °C.

11. The method of claim 10, wherein the reaction temperature is 0 °C to 50 °C.

12. The method of claim 7, further comprising:

before reacting the reagent in the presence of the superacid, adding the superacid and the reagent into a solvent, wherein the solvent comprises benzene, toluene, chlorobenzene, dichlorobenzene, dichloromethane, 1,2-dichloroethane, trichloromethane, or combinations thereof.

13. The method of claim 12, wherein the solvent is an anhydrous solvent.

14. The method of claim 7, wherein $R_1$ and $R_2$ have the same structures.

15. The method of claim 7, wherein $R_1$ and $R_2$ have different structures.

* * * * *